(12) United States Patent
Hanke

(10) Patent No.: US 9,119,840 B2
(45) Date of Patent: Sep. 1, 2015

(54) USE OF AN ACTIVE SUBSTANCE BINDING TO CD28 FOR PRODUCING A PHARMACEUTICAL COMPOSITION FOR ACTIVATING AND EXPANDING T CELLS

(71) Applicant: Theramab LLC, Wurzburg (DE)

(72) Inventor: Thomas Hanke, Wurzburg (DE)

(73) Assignee: THERAMAB LLC, Moscow (RU)

( * ) Notice: Subject to any disclaimer, the term of this patent is extended or adjusted under 35 U.S.C. 154(b) by 225 days.

(21) Appl. No.: 13/625,521

(22) Filed: Sep. 24, 2012

(65) Prior Publication Data

US 2013/0078257 A1   Mar. 28, 2013

Related U.S. Application Data

(63) Continuation of application No. 11/646,986, filed on Dec. 28, 2006, now abandoned, which is a continuation of application No. 10/988,207, filed on Nov. 12, 2004, now abandoned.

(30) Foreign Application Priority Data

Nov. 11, 2003 (DE) .................................. 103 52 900

(51) Int. Cl.
*A61K 39/395* (2006.01)
*C07K 16/28* (2006.01)

(52) U.S. Cl.
CPC ....... *A61K 39/39558* (2013.01); *C07K 16/2818* (2013.01); *C07K 2316/95* (2013.01)

(58) Field of Classification Search
None
See application file for complete search history.

(56) References Cited

FOREIGN PATENT DOCUMENTS

| DE | 197 22 888 A1 | 12/1998 |
|----|---|---|
| DE | 102 12 108 A1 | 10/2003 |
| WO | 9854225 A2 | 12/1998 |
| WO | 03078468 A2 | 9/2003 |

OTHER PUBLICATIONS

Wadman M., Nature, 2006, 440: 388-389.*
Hopkin M., Nature, 2006, 440: 855-856.*
Mehrishi et al., Vaccine, 2007, 25: 3517-3523.*
Elflein et al., Blood, 2003; 102:1764-1770.*
Voskoglou-Nomikos (Clin. Can. Res. 9:4227-4239 (2003)).
Dennis (Nature 442:739-741 (2006)).
Cespdes et al. (Clin. Transl. Oncol. 8(5):318-329 (2006)).
Seaver (Genetic Engineering 14(14):pp. 10 and 21 (1994)).
Suntharalingam et al. (NEJM 355:1018-1029 (2006)).
Goodyear (BMJ 333:270-271 (2006)).
Tufet (Nature Review Immunol. 8: 322 (May 2008)).
Muller et al. (J. Clin. Invest. 118:1405-1416 (Apr. 2008)).
Weirda W.G. et al., "CD40-ligand (CD154) gene therapy for chronic lymphocytic leukemia", Blood, Nov. 1, 2000, vol. 96, pp. 2917-2924.
Janeway C.A., Jr et al., Immunobiology: 5th ed., Garland Publishing, New York, 2001, http://www.ncbi.nlmnih.gov/books/bv.fcgi?call=bv.View..ShowSection&rid=imm, downloaded Oct. 8, 2004, 11pp.
Norderhaug L. et al., "Versatile vectors for transient and stable expression of recombinant antibody molecules in mammalian cells", Journal of Immunological Methods, vol. 204, Issue 1, May 12, 1997, pp. 77-87.
Ostrov D.A. et al., "Structure of Murine CTLA-4 and Its Role in Modulating T Cell Responsiveness", Science, Oct. 27, 2000, vol. 290, pp. 816-819.
Kato K. et al., "Gene transfer of CD40-ligand induces autologous immune recognition of chronic lymphocytic leukemia B cells", J Clin Invest, 101, 1998, pp. 1133-1141.
Wendtner C-M. et al., "Efficient gene transfer of CD40 ligand into primary B-CLL cells using recombinant adeno-associated virus (rAAV) vectors", Blood, Sep. 1, 2002, vol. 100, No. 5, pp. 1655-1661.
Scrivener S. et al., "Abnormal T-cell function in B-cell chronic lymphocytic leukaemia", Leuk Lymphoma, 2003, 44(3), pp. 383-389.
Caligaris-Cappio F., "Biology if Chronic Lymphocytic Leukemia", Reviews in Clinical and Experimental Hermatology, vol. 4, Issue 1, Mar. 2000, pp. 5-21.
Cantwell M. et al., "Gene Transfer of CD40-Ligand Induces Autologous Immune Recognition of Chronic Lymphocytic Leukemia B Cells", Nat Med 3, No. 9, Sep. 1997, pp. 984-989.
Landis S. H. et al., "Cancer statistics, 1999", CA Cancer J Clin, pp. 8-31.
Rozman C. et al. "Chronic lymphocytic leukemia", N Engl J Med, 333, 1995, pp. 1052-1057.
Tacke M. et al., "CD28-mediated induction of proliferation in resting T cells in vitro and in vivo without engagement or the T cell receptor: evidence for functionally distinct forms of CD28", Eur J Immunol, 1997, 27, pp. 239-247.

* cited by examiner

*Primary Examiner* — Ilia Ouspenski

(74) *Attorney, Agent, or Firm* — Morgan, Lewis & Bockius LLP

(57) ABSTRACT

The invention relates to the use of a superagonistic monoclonal antibody (mAb), which is specific for a naturally costimulatory receptor expressed on T cells, or a mimicry compound thereto, for producing a pharmaceutical composition for the treatment of diseases occurring with lacking costimulability of T cells, in particular of the B-CLL.

8 Claims, 12 Drawing Sheets

AS SEQUENCE OF THE HC OF TGN1412 INCLUDING LEADER PEPTIDE

⎡── LEADER ──⎤

MGWSCIILFLVATATGVHSQVQLVQSGAEVKKPGASVKVSCKASGYTFTSYYIHWVRQAPGQ

GLEWIGCIYPGNVNTNYNEKFKDRATLTVDTSISTAYMELSRLRSDDTAVYFCTRSHYGLDW

VHC (SEQ ID NO: 19)

NFDVWGQGTTVTVSSASTKGPSVFPLAPCSRSTSESTAALGCLVKDYFPEPVTVSWNSGALT

SGVHTFPAVLQSSGLYSLSSVVTVPSSSLGTKTYTCNVDHKPSNTKVDKRVESKYGPPCPSC

PAPEFLGGPSVFLFPPKPKDTLMISRTPEVTCVVVDVSQEDPEVQFNWYVDGVEVHNAKTKP ← CHC (SEQ ID NO: 24)

REEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK

POSSIBLE VARIANTS AT THE C TERMINUS (NO IMPAIRMENT OF FUNCTION)

(...) SLGK OR (...) SLGKK OR (...) SLG

LEADER PEPTIDE

MGWSCIILFLVATATGVHS (SEQ ID NO: 20)

FIG. 9a

DNA SEQUENCE OF THE HC OF TGN1412 INCLUDING INTRONS, UTR'S AND LEADER PEPTIDE

```
   1 ggtaccgggc cgacctcacc atgggatgga gctgtatcat cctcttcttg gtagcaacag
  61 ctacaggtaa ggggctcaca gtagcaggct tgaggtctgg acatatatat gggtgacaat
 121 gacatccact ttgcctttct ctccacaggt gtgcattccc aggtgcagct ggtgcagtct
 181 ggggctgagg tgaagaagcc tggggcctca gtgaaggtct cctgcaaggc ttctggatac
 241 accttcacca gctactatat acactgggtg cgacaggccc ctggacaagg gcttgagtgg
 301 attggatgta ttcatcctgg aatgtcaat actaactata atgagaagtt caaggacagg
 361 gccaccctga ccgtagacac gtccatcagc acagcctaca tggagctgag caggctgaga
 421 tctgacgaca cggccgtgta tttctgtaca agatcacact acggcctcga ctggaacttc
 481 gatgtctggg gccaagggac cacggtcacc gtctcctcag gtgagtcgta cgctagcaag
 541 ctttctgggg caggccgggc ctgactttgg ctgggggcag ggagggggct aaggtgacgc
 601 aggtggcgcc agccaggtgc acacccaatg cccatgagcc cagacactgg accctgcatg
 661 gaccatcgcg gatagacaag aaccgagggg cctctgcgcc ctgggcccag ctctgtccca
 721 caccgcggtc acatggcacc acctctcttg cagcttccac caagggccca tcggtcttcc
 781 ccctggcgcc ctgctccagg agcacctccg agagcacagc cgccctgggc tgcctggtca
 841 aggactactt ccccgaaccg gtgacggtgt cgtggaactc aggcgccctg accagcggcg
 901 tgcacacctt cccggctgtc ctacagtcct caggactcta ctccctcagc agcgtggtga
 961 ccgtgccctc cagcagcttg ggcacgaaga cctacacctg caacgtagat cacaagccca
1021 gcaacaccaa ggtggacaag agagttggtg agaggccagc acagggaggg agggtgtctg
1081 ctggaagcca ggctcagccc tcctgcctgg acgcaccccg gctgtgcagc cccagcccag
1141 ggcagcaagg catgccccat ctgtctcctc acccggaggc ctctgaccac cccactcatg
1201 ctcagggaga gggtcttctg gatttttcca ccaggctccg ggcagccaca ggctggatgc
1261 ccctacccca ggccctgcgc atacaggggc aggtgctgcg ctcagacctg ccaagagcca
1321 tatccgggag gaccctgccc ctgacctaag cccaccccaa aggccaaact ctccactccc
1381 tcagctcaga caccttctct cctcccagat ctgagtaact cccaatcttc tctctgcaga
1441 gtccaaatat ggtcccccat gcccatcatg cccaggtaag ccaacccagg cctcgccctc
1501 cagctcaagg cgggacaggt gccctagagt agcctgcatc cagggacagg ccccagccgg
1561 gtgctgacgc atccacctcc atctcttcct cagcacctga gttcctgggg ggaccatcag
1621 tcttcctgtt ccccccaaaa cccaaggaca ctctcatgat ctcccggacc cctgaggtca
1681 cgtgcgtggt ggtggacgtg agccaggaag accccgaggt ccagttcaac tggtacgtgg
1741 atggcgtgga ggtgcataat gccaagacaa agccgcggga ggagcagttc aacagcacgt
1801 accgtgtggt cagcgtcctc accgtcctgc accaggactg gctgaacggc aaggagtaca
1861 agtgcaaggt ctccaacaaa ggcctcccgt cctccatcga gaaaaccatc tccaaagcca
1921 aaggtgggac ccacggggtg cgagggccac atggacagag gtcagctcgg cccaccctct
1981 gccctgggag tgaccgctgt gccaacctct gtccctacag ggcagccccg agagccacag
2011 gtgtacaccc tgcccccatc ccaggaggag atgaccaaga accaggtcag cctgacctgc
2101 ctggtcaaag gcttctaccc cagcgacatc gccgtggagt gggagagcaa tgggcagccg
2161 gagaacaact acaagaccac gcctcccgtg ctggactccg acggctcctt cttcctctac
2221 agcaggctaa ccgtggacaa gagcaggtgg caggagggga atgtcttctc atgctccgtg
2281 atgcatgagg ctctgcacaa ccactacaca cagaagagcc tctccctgtc tctgggtaaa
2341 tgagtgccag ggccggcaag cccccgctcc ccgggctctc ggggtcgcgc gaggatgctt
2401 ggcacgtacc ccgtctacat acttcccagg cacccagcat ggaaataaag cacccaccac
2461 tgccctgggc ccctgtgaga ctgtgatggt tctttccacg ggtcaggccg agtctgaggc
2521 ctgagtgaca tgagggaggc agagcggatc c   (SEQ ID NO:28)
```

POS. 21 atg: 1. LEADER CODON (LEADER WITH INTRON)

POS. 157 tcc: LAST LEADER CODON

POS. 160 cag: 1. VHR-CODON

POS. 517 tca: LAST VHR-CODON

POS. 2338 aaa: LAST IgG4 CONSTANT CODON

POS. 2341 tga: STOP

FIG. 9c

DNA SEQUENCE OF THE LC OF TGN1412 INCLUDING
INTRONS, UTR'S AND LEADER PEPTIDE

```
   1 ggtaccgggc cgacctcacc atgggatgga gctgtatcat cctcttcttg gtagcaacag
  61 ctacaggtaa ggggctcaca gtagcaggct tgaggtctgg acatatatat gggtgacaat
 121 gacatccact ttgctttbct ctccacaggt gtgcattccg acatccagat gacccagtct
 181 ccatcctccc tgtctgcatc tgtaggagac agagtcacca tcacttgcca tgccagtcaa
 241 aacatttatg ttggttaaac tggcatcag cagaaaccag ggaaagcccc taagctcctg
 301 atctataagg cttccaacct gcacacaggg gtcccatcaa ggttcagtgg cagtggatct
 361 gggacagatt tcactctcac catcagcagt ctgcaacctg aagattttgc aacttactac
 421 tgtcaacagg gtcaaactta tccgtacacg ttcggcggag ggaccaaggt ggagatcaaa
 481 cgtgagtcgt acgctagcaa gcttgatatc gaattctaaa ctctgagggt gtcggatgac
 541 gtggccattc tttgcctaaa gcattgagtt tactgcaagg tcagaaaagc atgcaaagcc
 601 ctcagaatgg ctgcaaagag ctccaacaaa acaatttaga actttattaa ggaataggg
 661 gaagctagga agaaactcaa aacatcaaga ttttaaatac gcttcttggt ctccttgcta
 721 taattacctg ggataagcat gctgttttct gtctgtcct aacatgccct gtgattatcc
 781 gcaaacaaca cacccaaggg cagaacttg ttacttaaac accatcctgt ttgcttcttt
 841 actcaggaac tgtggctgca ccatctgtct tcatcttccc gccatctgat gagcagttga
 901 aatctggaac tgcctctgtt gtgtgcctgc tgaataactt ctatcccaga gaggccaaag
 961 tacagtggaa ggtggataac gccctccaat cgggtaactc ccaggagagt gtcacagagc
1021 aggacagcaa ggacagcacc tacagcctca gcagcaccct gacgctgagc aaagcagact
1081 acgagaaaca caaagtctac gcctgcgaag tcacccatca gggcctgagc tcgcccgtca
1141 caaagagctt caacagggga gagtgttaga gggagaagtg cccccacctg ctcctcagtt
1201 ccagcctgac ccctccccat cctttggcct ctgaccctt tccacaggg gacctaccc
1261 tattgcgytt ctccagctca tcttcacct cacccccctc ctcctccttg gctttaatta
1321 tgctaatgtt ggaggagaat gaataaataa agtgaatctt tgcacctgtg gtttctctct
1381 ttcctcattt aataattatt atctgttgtt ttaccaacta ctcaatttct cttataaggg
1441 actaaatatg tagtcatcct aaggcgcata accatttata aaatcatcc ttcattctat
1501 tttaccctat catcctctgc aagacagtcc tccctcaaac cccaaagcct ctgtcctca
1561 cagtccctg ggccatggta ggagagactt gcttcttgt ttccccctcc tcagcaagcc
1621 ctcatcagtcc tttttaaggg tgacaggtct tacagtcata tatccttga ttcaattccc
1681 tgagaatcaa ccaaagcaaa ttcctgcagc tcggggatc c
```
(SEQ ID NO:27)

POS. 21 atg: 1. LEADER CODON        POS. 157 tcc: LAST LEADER CODON
(LEADER WITH INTRON!)

POS. 160 gac: 1. VLR CODON           POS. 478 aaa: LAST VLR CODON

POS. 1184 tgt: LAST KAPPA CONSTANT CODON

POS. 1187 tag: STOP

FIG. 9d

USE OF AN ACTIVE SUBSTANCE BINDING TO CD28 FOR PRODUCING A PHARMACEUTICAL COMPOSITION FOR ACTIVATING AND EXPANDING T CELLS

STATEMENT OF RELATED APPLICATIONS

This application is a continuation of co-pending U.S. patent application Ser. No. 11/646,986, filed Dec. 28, 2006, which is a continuation of U.S. patent application Ser. No. 10/988,207, filed Nov. 12, 2004, each of which is incorporated herein by reference in its entirety.

FIELD OF THE INVENTION

The invention relates to the use of an active substance for producing a pharmaceutical composition for the treatment of chronic lymphocytic leukemia of the B-cell type (B-CLL).

BACKGROUND OF THE INVENTION AND PRIOR ART

For understanding the invention, firstly the following terminological background is important. The activation of resting T cells for proliferation and functional differentiation firstly requires the occupation of two surface structures, so-called receptors: 1. of the antigen receptor having a different specificity from cell to cell and being necessary for detecting antigens, for instance viral fission products; and 2. of the CD28 molecule equally expressed on all resting T cells with the exception of a sub-group of the CD8 T cells of man, the CD28 molecule naturally binding to ligands on the surface of other cells of the immune system. This is the "costimulation" of the antigen-specific immune reaction by CD28. In a cell culture, these processes can be simulated by occupation of the antigen receptor and of the CD28 molecule with suitable monoclonal antibodies (mAb's). In the classic system of costimulation, neither the occupation of the antigen receptor nor that of the CD28 molecule alone will lead to a T cell proliferation, the occupation of both receptors is however effective. This observation was made in T cells of humans, mouse and rat.

There are however also known CD28-specific mAb's that can initiate the T cell proliferation without costimulation. Such a superagonistic, i.e. independent from the occupation of the antigen receptor, activation of resting T lymphocytes by CD28-specific mAb's is known in the art from the document Tacke et al., Eur. J. Immunol., 1997, 27:239-247. According thereto, two types of CD28-specific monoclonal antibodies having different functional properties are described: costimulatory mAb's costimulating the activation of resting T cells only with simultaneous occupation of the antigen receptor; and superagonistic mAb's, which can activate T lymphocytes of all classes in vitro and in the test animal for proliferation without occupation of the antigen receptor. From the documents DE 197 22 888 and PCT/DE03/00890 are also known CD28-specific mAb's, which efficiently activate T lymphocytes in vitro as well as in vivo without TCR stimulation, i.e. which act "superagonistically". The mAb's, at least those, which are directed against human CD28, are also called SuperMAb's.

The chronic lymphatic leukemia of the B-cell series (chronic lymphocytic leukemia of the B-cell type, B-CLL) is with an incidence of 3 per 100,000 inhabitants the most frequent leukemia of adults (Landis et al., 1999). The disease is characterized by a progressive accumulation of malignant monoclonal B lymphocytes in the blood, lymph nodes, liver and bone marrow. With progressing disease, the lymphocyte count in the blood will be increased, lymph nodes, liver and spleen will become enlarged, and an anemia and thrombocytopenia will occur (Caligaris-Cappio, 2000; Rozman and Montserrat, 1995). A curative therapy of the B-CLL is not possible at present.

To the main complications of the B-CLL belong infections, for which can be blamed, among other reasons, the T cell defects or low T cell counts to be observed in many patients (Cantwell et al., 1997; Scrivener et al., 2003).

A limited function can further also be found in the tumor cells themselves. The property of the B-CLL B cells, to act as antigen-presenting cells (APC's) and to thus be detected and eliminated by tumor-specific T cells, is substantially limited. The reason for this, among others, is that B-CLL B cells do not express or only insufficiently express the natural CD28 ligands CD80 (=B7.1) and CD86 (=B7.2) at their cell surface. Thus the potentially tumor-specific T cells will obtain a single signal only for the interaction between the T cell receptor and MHC+tumor antigen and not the second costimulatory signal necessary for the full activation of a T cell. As a summary, this indicates that the immune system of B-CLL patients obviously is not capable of eliminating the tumor cells by itself.

One approach for therapy aims for improving the APC function of the B-CLL B cells and thus reinforcing the anti-tumor immune response of the patient. Various working groups have already tried to specifically activate B-CLL B cells and to thereby induce the expression of costimulatory ligands. They were successful in expressing, by gene transfer, the B cell stimulating CD40 ligand (CD40L) in the B-CLL B cells, and thus making possible the interaction between CD40L and the protein CD40 being present on all B cells (including the B-CLL B cells). The signal forwarded by CD40 into the cell interior led to the desired expression of the costimulatory ligand CD80 and CD86 (Kato et al., 1998; Wendtner et al., 2002). The leukemia cells thus modified could now in fact act in a more efficient way than APC's, and were now also eliminated—firstly in vitro—by autologous T cells (Kato et al., 1998). The in vivo gene transfer of CD40L was also effective: it led in the patients to an increase in the T cell count as well as to a reduction of the leukemic cells (Wierda et al., 2000). This therapeutic approach does not influence, however, the above mentioned T cell defects of the B-CLL disease.

In the following is shown the bibliography of the above scientific literature. Caligaris-Cappio, F., Rev Clin Exp Hematol 4, 5-21 (2000); Cantwell, M. et al., Nat Med 3, 984-989 (1997); Kato, K. et al., J Clin Invest 101, 1133-1141 (1998); Landis, S. H. et al., CA Cancer J Clin 49, 8-31 (1999); Rozman, C. et al., N Engl J Med 333, 1052-1057 (1995); Scrivener, S. et al., Leuk Lymphona 44, 383-389 (2003); Wendtner, C. M. et al., Blood 100, 1655-1661 (2002); Wierda, W. G. et al., Blood 96, 2917-2924 (2000).

TECHNICAL OBJECT OF THE INVENTION

It is the technical object of the invention to provide a pharmaceutical composition, by means of which B-CLL can be treated, and whereby simultaneously the immune system weakened by the disease, in particular the T cell-mediated cellular immunity, is generally improved.

BRIEF DESCRIPTION OF THE DRAWINGS

FIGS. 9A and 9B show the amino acid sequences of the heavy chain (SEQ ID NOS:19 and 24) and light chains, (SEQ ID NOS: 21 and 25) of the monoclonal antibody, TGN1412, and a leader peptide (SEQ ID NO:20).

FIGS. 9C and 9D are nucleotide sequences of cDNA's coding for the heavy chain (SEQ ID NO:28) and light chain (SEQ ID NO:27) of the monoclonal antibody, TGN1412, inserted into plasmids pLNOH and pLNOK.

BASICS OF THE INVENTION AND PREFERRED EMBODIMENTS

Figure 1:
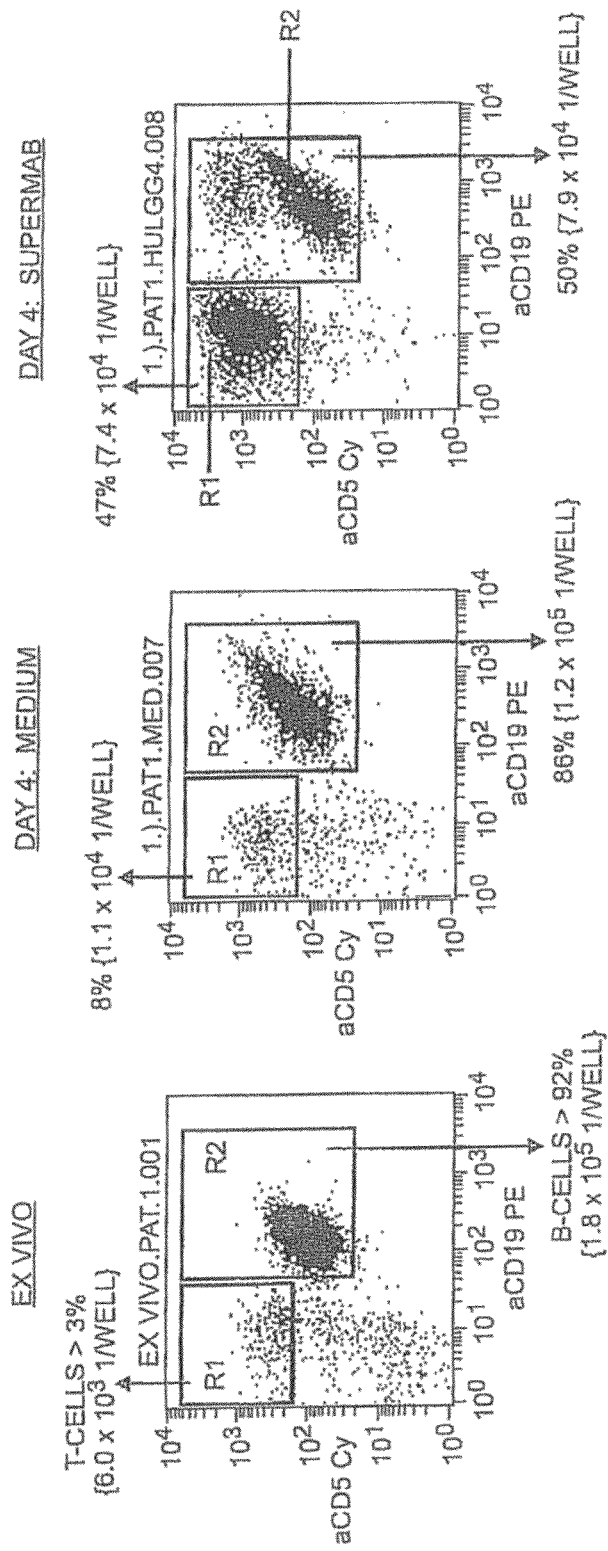
FIG. 1 is a schematic representation of a dot-dot analysis showing B-CLL T Cell expansion upon induction with SuperMAB.

For achieving this technical object, the invention teaches the use of a superagonistic monoclonal antibody (mAb), which is specific for a naturally costimulatory receptor expressed on resting T cells, in particular a CD28, CTLA-4, ICOS or PD1-specific superagonistic mAb, or a mimicry compound thereto, for producing a pharmaceutical composition for the treatment of diseases lacking costimulability of T cells, in particular of chronic lymphocytic leukemia of the B-cell type (B-CLL). Other diseases lacking costimulability of T cells are for instance agammaglobulinemia, selective immunoglobulin deficiencies, such as selective IgA deficiency, common variable immunodeficiencies (CVID), diseases, where compared to solid tumors such as lung carcinoma, the capability of tumor-specific T cells is limited due to the lack of expression of costimulatory ligands on tumor cells, to cytotoxically react against the tumor cells, and where T cells are made capable, by superagonistic CD28 stimulation, to cytotoxically react.

The invention is based on the finding that with the use of the mAb's according to the invention a double effect so to speak is obtained. On the one hand, normal T cells, which are repressed because of the disease, are activated or expanded. Thereby, often highly critical infections can be prevented or reduced in the course of the disease. Simultaneously, the body-own immune system is excited to eliminate the B-CLL B cells normally not or only weakly attacked by tumor-specific T cells. This is achieved in that the B-CLL B cells are activated to present a costimulatory ligand not normally expressed by them. Thus, the body-own tumor-specific T cells reliant upon such a signal are able to effectively attack the B-CLL B cells.

An mAb according to the invention can, for instance, be produced by immunizing a non-human mammal with CD28 or a partial sequence thereof, for instance the C'-D loop, wherein from the non-human mammal cells are taken, and from the cells hybridoma cells are produced, and wherein the thus obtained hybridoma cells are selected such that there are contained mAb's superagonistically binding to CD28 in their culture supernatant. However, other common methods for obtaining corresponding mAb's can also be used, such as phage display or human-Ig transgenic mice. Suitable mAb's can also be produced by that B lymphocytes are selected, which superagonistically bind to CD28 or its C'-D loop, and its expressed immunoglobulin genes are cloned. For ICOS, CTLA-4 and PD1 corresponding considerations apply.

In principle, the mAb's used according to the invention may also be antibodies derived from the described mAb's, such as chimeric or genetically humanized antibodies.

An active substance according to the invention binds to CD28, CTLA-4, ICOS or PD1, in particular CD28 or ICOS, or to a partial sequence therefrom. The CD28 partial sequence may for instance contain an amino acid sequence SEQ ID NO: 1, or 2-7, or 17, which is located at least in part in the region of the C'-D loop of CD28. At one of the sequences with val at the 5' terminal, one or several amino acids of the sequence 8 may be connected in the order defined there. The loop is in the region with the sequence GNYSQQLQVYSK-TGF (SEQ ID NO:17). The binding may however also take place at other partial sequences of the region of the C'-D loop, and reference is made to the definition of the region of the C'-D loop. There are for instance also mentioned possible sequences from CTLA-4, ICOS and PD1.

Mimicry compounds according to the invention can be identified in a screening method, wherein a prospective mimicry compound or a mixture of prospective mimicry compounds are subjected to a binding assay with CD28, CTLA-4, ICOS or PD1 or to a partial sequence therefrom, for instance, as mentioned above, and wherein active substances binding to CD28, CTLA-4, ICOS, or PD1 or to the partial sequence therefrom are selected, if applicable followed by an assay for testing for superagonistic stimulation of several to all subgroups of the T lymphocytes. In the case of a mixture, it will be suitable to perform a deconvolution. Among the selected mimicry compounds, so to speak a ranking according to the selectivity and/or affinity may take place, with highly affinitive active substances being preferred.

The mAb may, for instance, be obtained from hybridoma cells, as filed under the DSM numbers DSM ACC2531 (mAb: 9D7 or 9D7G3H11) or DSM ACC2530 (mAb: 5.11A or 5.11A1C2H3). The mAb or the mimicry compound preferably contains one or several sequences SEQ ID NOS: 9, 11, 13 and/or 15, or one or several sequences SEQ ID NOS: 10, 12, 14 and/or 16, or one or several sequences 18 and/or 19, or sequences being homologous thereto.

Figure 9B:
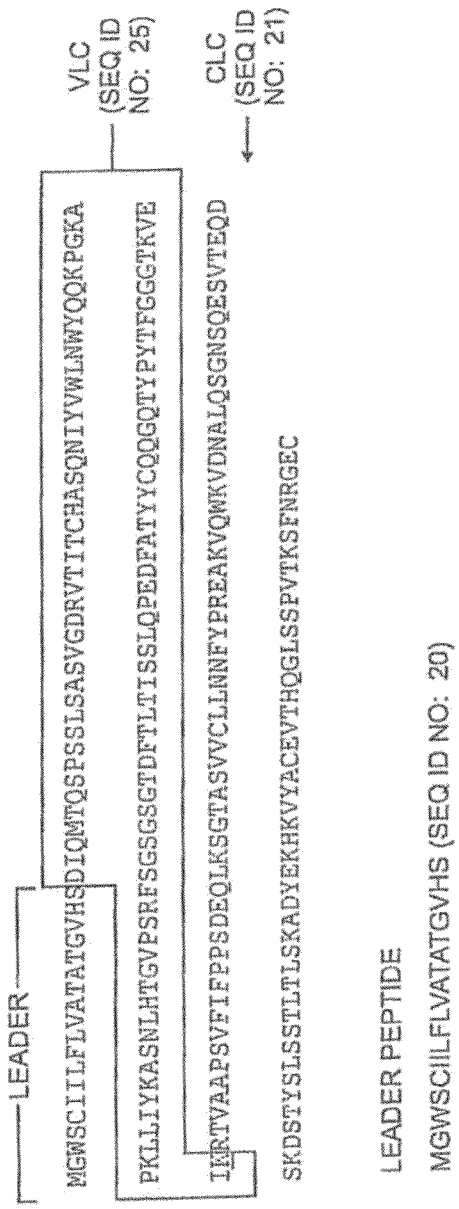

Another mAb TGN1412 with improved properties suitable for the purpose of the invention contains as the variable region of the heavy chain (VHC) the amino acid sequence of FIG. 9a and as the variable region of the heavy chain the amino acid sequence of FIG. 9b. The leader peptides cited in FIGS. 9a and 9b are irrelevant for the function of the mAb and solely serve for making the passage of the antibodies through the cell membrane easier. The variants of the C terminus shown in the figures do not lead to a change in the function of the antibodies.

The invention further relates (among other countries, for the U.S.A.) to a method for the treatment of in particular B-CLL, wherein either to a patient is administered a pharmaceutical composition comprising a superagonistic monoclonal antibody used according to the invention or a mimicry compound thereto and galenically prepared for a defined and employed dosage form, for instance IV injection, or from a patient is taken a body liquid (=cell suspension), in particular blood, comprising T lymphocytes and/or forerunner cells thereto, the body liquid, if applicable after a preparation step, is reacted with a superagonistic monoclonal antibody used according to the invention or a mimicry compound thereto, and the thus treated body liquid is again administered to the patient, for instance IV injected.

It may be advisable, prior to the treatment, to take a blood sample from a patient diseased with B-CLL, to cultivate in vitro PBMC's included therein, to incubate the culture with mAb's used according to the invention, and to determine the activation of T cells and/or the elimination or reduction of B-CLL B cells. With regard to a possible determination method, reference, for instance, is made to the embodiments, of course other usual determination methods and the means used therefor are also suitable. In so far, the invention also comprises a test kit for testing for the therapeutic effectivity of a prospective treatment of B-CLL with a pharmaceutical composition according to the invention with the following components: i) means for PBMC cultivation in vitro; ii) a preparation comprising mAb's according to the invention in a physiologically effective dose; iii) means for determining the T cell counts or the activation and/or means for determining the B-CLL B cell counts.

The administered daily dose for the indication B-CLL may be in the range of 0.1 to 50, preferably 1 to 10 mg/kg body weight.

The invention finally relates to a method for reducing (in vivo) B-CLL B cells and expanding T cells in a liquid containing normal T cells, B cells and B-CLL B cells, wherein by interaction of the normal T cells present in the liquid with a superagonistic mAb used according to the invention or a mimicry compound thereto, the normal T cells are activated or expanded, and wherein by interaction of the B-CLL T cells present in the liquid with the superagonistic CD28-specific mAb or the mimicry compound thereto or a superagonistic mAb different therefrom or a mimicry compound different therefrom are activated to the expression of a CD40 ligand and if applicable expanded, wherein the activated or expanded B-CLL T cells carrying CD40 ligands induce the expression of CD86 and/or CD80 in B-CLL B cells carrying CD40, wherein autologous tumor-specific T cells are costimulatorily activated or expanded by the B-CLL B cells carrying CD86 and/or CD80, and wherein the activated tumor-specific T cells eliminate the B-CLL B cells.

DEFINITIONS

Monoclonal antibodies (mAb's) are antibodies, which are produced by hybrid cell lines (so-called hybridomas) typically generated by fusion of a B cell of animal or human origin producing antibodies with a suitable myeloma tumor cell.

The amino acid sequence of human CD28 is known under the accession No. NM_006139. The amino acid sequence of human CTLA-4 is known under the accession No. L15006. The amino acid sequence of human ICOS is known under the accession No. AJ277832. The amino acid sequence of human PD1 is known under the accession No. U64863.

The C'-D loop of CD28 comprises the amino acids 43 to 70, in particular 52 to 66 of the above CD28 sequence (for numbering see also Ostrov, D. A., et al.; Science (2000), 290:816-819). The term C'-D loop will in the following also include any partial sequences therefrom. The term region of the C'-D loop comprises in addition to or in lieu of the C'-D loop spatially adjacent regions of the CD28. These are according to the above numbering system in particular the amino acids 78 (Tyr) to 87 (Thr). With regard to partial sequences in CTLA-4, ICOS and PD1 corresponding to the CD28 C'-D loop, reference is made to the document DE-101 60 516 A1, in particular FIG. 7 and text belonging thereto and sequence information given there.

A loop or a binding site arranged therein is freely accessible, if for a defined binding partner for the binding site in the loop there is no steric hindrance by the sequences or molecules following to the loop.

Activation and/or expansion of T cells is the increase of metabolic activity, enlargement of the cell volume, synthesis of immunologically important molecules, such as CD40 ligand, and initiation of the cell division (proliferation) upon an external stimulus. As a result, there are more T cells after the activation or expansion than before.

Homology is at least 70%, preferably at least 80%, most preferably at least 90% sequence identity on a protein level, a homologous protein or peptide binding a defined binding partner with at least identical affinity. Deviations in the sequence may be deletions, substitutions, insertions and elongations.

A mimicry compound is a natural or synthetic chemical structure behaving in a defined binding assay as a defined mAb mimicried by the mimicry compound.

The term "mAb's" comprises, in addition to structures of the conventional Fab/Fc type, also structures exclusively consisting of the Fab fragment. It is also possible to use the variable region only, the fragment of the heavy chains being connected with the fragment of the light chain in a suitable manner, for instance also by means of synthetic bridge molecules. The term antibody also comprises (possibly complete) chimeric and genetically humanized antibodies.

Superagonistic stimulation of the proliferation of CD28-specific T cells means that no costimulation, i.e. no further binding event in addition to a binding of an mAb or of a mimicry compound to CD28 is necessary for the stimulation or inhibition of the proliferation.

In the following, the invention is explained in more detail with reference to embodiments representing examples only.

Example 1

SuperMAB Induces the In Vitro Expansion of B-CLL T Cells

In a first experiment, peripheral mononuclear cells were isolated from the blood (PBMC's) of a B-CLL patient, and $2 \times 10^5$ cells each were cultivated in 96-well microtiter plates at 37° C. either in medium only or in the presence of SuperMAB (0.5 µg/ml in solution). After four days, the total cell count was determined in the Neubauer counting chamber. Further, the cells were incubated with fluorescence-marked monoclonal antibodies with specificity for CD19 (B cell marker) and CD5 (expressed on B-CLL B cells and T cells) and analyzed in the FACS. FIG. 1 shows a so-called dot blot analysis. Every dot represents an analyzed cell and is localized according to the expression of CD19 (x axis) and CD5 (y axis). R1 marks the population of the T cells (CD19-CD5+), R2 the population of the B-CLL B cells (CD19+CD5+). FIG. 1 shows that SuperMAB is capable to induce a massive expansion of the B-CLL T cells. Whilst in the processes "ex vivo" and "medium" the T cells represent only 3% and 8%, resp., of the total population, this portion increased in the SuperMAB-treated cells to 47%. The analysis of the total cell counts showed that this is not only a relative, but also an absolute increase of T cells. Starting from $6 \times 10^3$ T cells/well (ex vivo) or 1.1×10^4 T cells/well (medium), resp., the addition of SuperMAB to the culture led to an increase to 7.4× 10^4 T cells/well. In the SuperMAB cultures, not only a proliferation of the tumor cells could be avoided, but also a reduction of these cells by approx. 50% could be achieved.

In further experiments, it was investigated now whether the expansion of the T cells induced by SuperMAB is also accompanied by qualitative changes, and can at last strengthen the immune response in B-CLL patients.

Example 2

Figure 2:
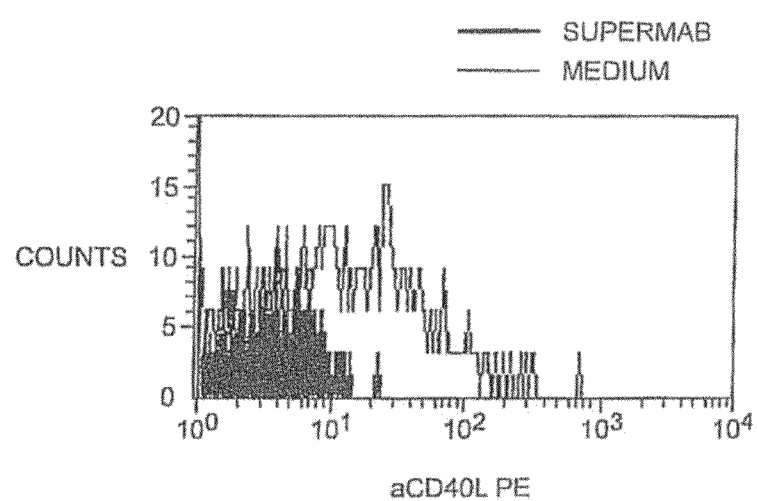
FIG. 2 is a schematic representation of a histogram showing the expression of CD40L on T cells as a function of cell count.

SuperMAB Induces the Expression of the B Cell-Stimulating CD40 Ligand on the Surface of B-CLL T Cells In earlier experiments it could already be shown that SuperMAB is capable to induce the expression of the B cell-stimulating CD40 ligand. It was now of interest whether this is also possible for T cells of B-CLL patients, and whether thus B-CLL B cells can be activated by a CD40L-CD40 interaction (see above). As described above, PBMC's of a B-CLL patient were cultivated in the presence or the absence of SuperMAB and stained after one day with a fluorescence-marked antibody with specificity for CD40L. FIG. 2 shows a so-called histogram, in which the expression of CD40L on the T cells (x axis: since PBMC's are a mixed culture, the T cells were limited before by a so-called "electronic gate") is shown as a function of the cell count (y axis). Compared to cells, which are only cultivated in medium, the T cells of the SuperMAB-treated culture showed a clearly stronger expression of CD40L. Thus, in principle the conditions are met that the T cells now expressing CD40L interact with the CD40 on the B-CLL B cells, and can thus induce the expression of costimulating ligands on these cells.

Example 3

Figure 3:
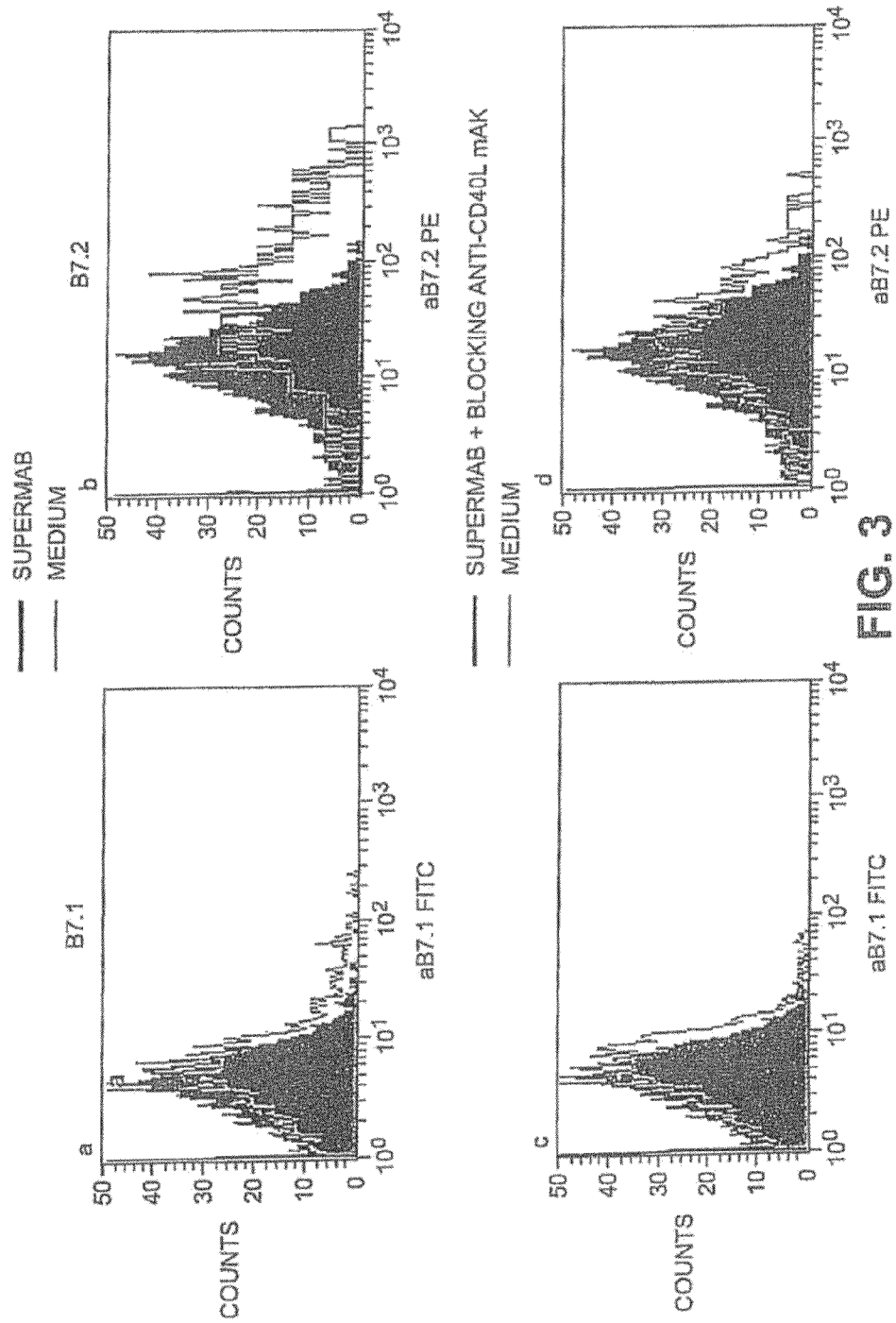
FIG. 3 are schematic representations of histograms showing the expression of B7.1 and B7.2 on B-CLL B cells.

SuperMAB Induces the Expression of the Costimulating Ligand B7.2 on B-CLL B Cells PBMC's of a B-CLL patient were cultivated as described above and stained after 4 days with fluorescence-marked monoclonal antibodies with specificity for B7.1 and B7.2. The histograms in FIG. 3 show the expression of these two proteins on the B-CLL B cells: whilst SuperMAB only moderately induced B7.1 on these cells (histogram a), it could drastically increase the expression of B7.2 (histogram b). In order to be able to show that the induction of B7.2 is the consequence of the expression of CD40L on SuperMAB-treated T cells shown in FIG. 2, in an additional process a blocking antibody (10 μg/ml) with specificity for CD40L was given into the cultures. As a consequence of its ability to block the interaction between CD40L and CD40, thus the induction of B7.2 on B-CLL B cells should also be prevented. The drastically reduced expression of B7.2 in the thus treated cells (histogram d) in fact shows that the blocking of CD40L prevents the induction of B7.2 on B-CLL B cells. This result thus provided the indirect proof that CD40L-expressing T cells activated by SuperMAB interact with CD40 on the surface of B-CLL B cells and can therefore induce the expression of costimulating proteins.

Example 4

SuperMAB Improves the Antigen-Presenting Function of B-CLL B Cells (Allogeneic Mixed Lymphocyte Culture)

Figure 4:
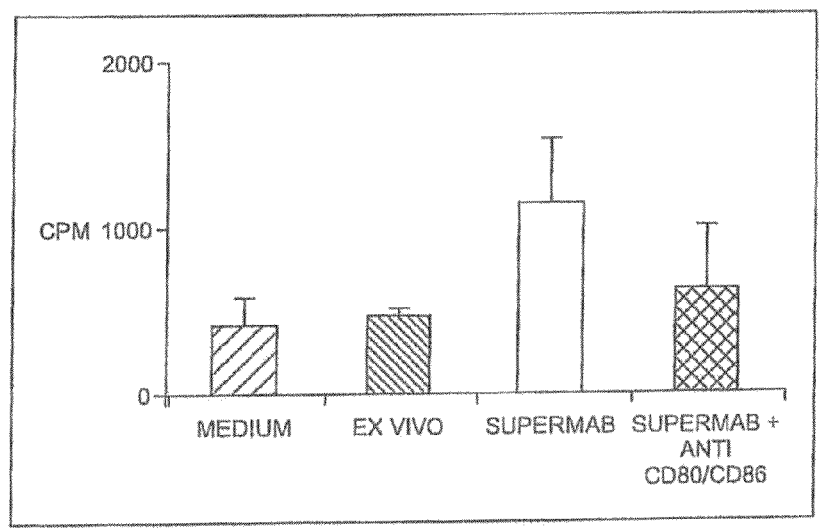
FIG. 4 is a graphical representation showing the proliferation of SuperMAB B-CLL B cells and not-SuperMAB-pretreated B-CLL B Cells.
Figure 6:
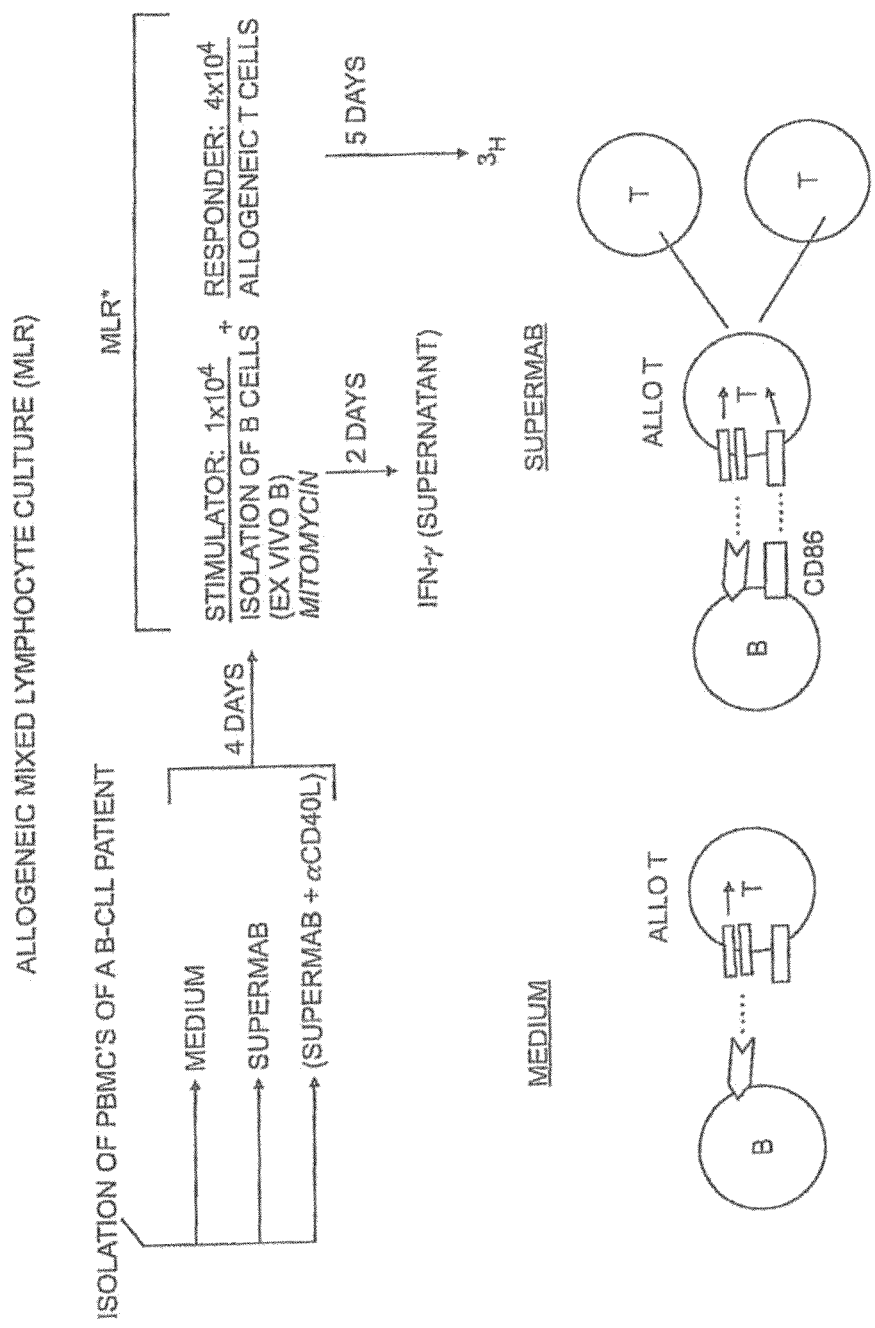
FIG. 6. is a diagrammatic representation showing T cell proliferation as measured by the incorporation of 3H thymidine.

The decisive question whether the expression of costimulatory ligands on the B-CLL B cells also occurs with an improved antigen-presenting function, can only be answered by functional tests: in the mixed lymphocyte culture, T cells of a person (=responder cells) are cultivated together with so-called stimulator cells. The stimulator cells are mitomycin C-treated cells of a second not related person (=allogeneic donor), which differs in the expression pattern of the genes of the major histocompatibility complex (MHC) from the first person. The T cells detect the foreign MHC proteins together with the costimulating ligands on the surface of the stimulator cells and are excited to proliferation (because of mitomycin C treatment, the stimulator cells cannot divide anymore). After four days, the T cell proliferation is measured by the incorporation of 3H thymidine (see FIG. 6). For answering the question, PBMC's of B-CLL patients were isolated and cultivated in medium or with SuperMAB (see above). After four days, the B-CLL B cells were separated from these cultures by magnetic separation, incubated with mitomycin C (60 μg/ml) for 1 h at 37° C., and served then as stimulator cells in the subsequent mixed lymphocyte culture: For this purpose, 1×10^4 stimulator cells were cultivated four five days with 4×10^4 T cells of an allogeneic donor (=responder cells), and the proliferation of the T cells was measured by the incorporation of 3H thymidine during the last 16 h (see FIG. 6). FIG. 4 shows that not-SuperMAB-pretreated B-CLL B cells (processes medium/ex vivo) can only cause a very weak proliferation of the indicator cells, which could substantially, i.e. by at least the factor 2, be increased by the addition of SuperMAB (process SuperMAB). By the addition of blocking monoclonal antibodies with specificity for B7.1 and B7.2 (5 μg/ml each; process SuperMAB+anti CD80/86), the proliferation could be reduced nearly to the level of the cells pretreated in the medium. As a summary can be said that these results make obvious that SuperMAB improves the antigen-preventing function of the B-CLL B cells by induction of the costimulatory proteins B7.1 and B7.2.

Example 5

SuperMAB Improves the Antigen-Presenting Function of B-CLL B Cells (Autologous Mixed Lymphocyte Culture)

Figure 7:
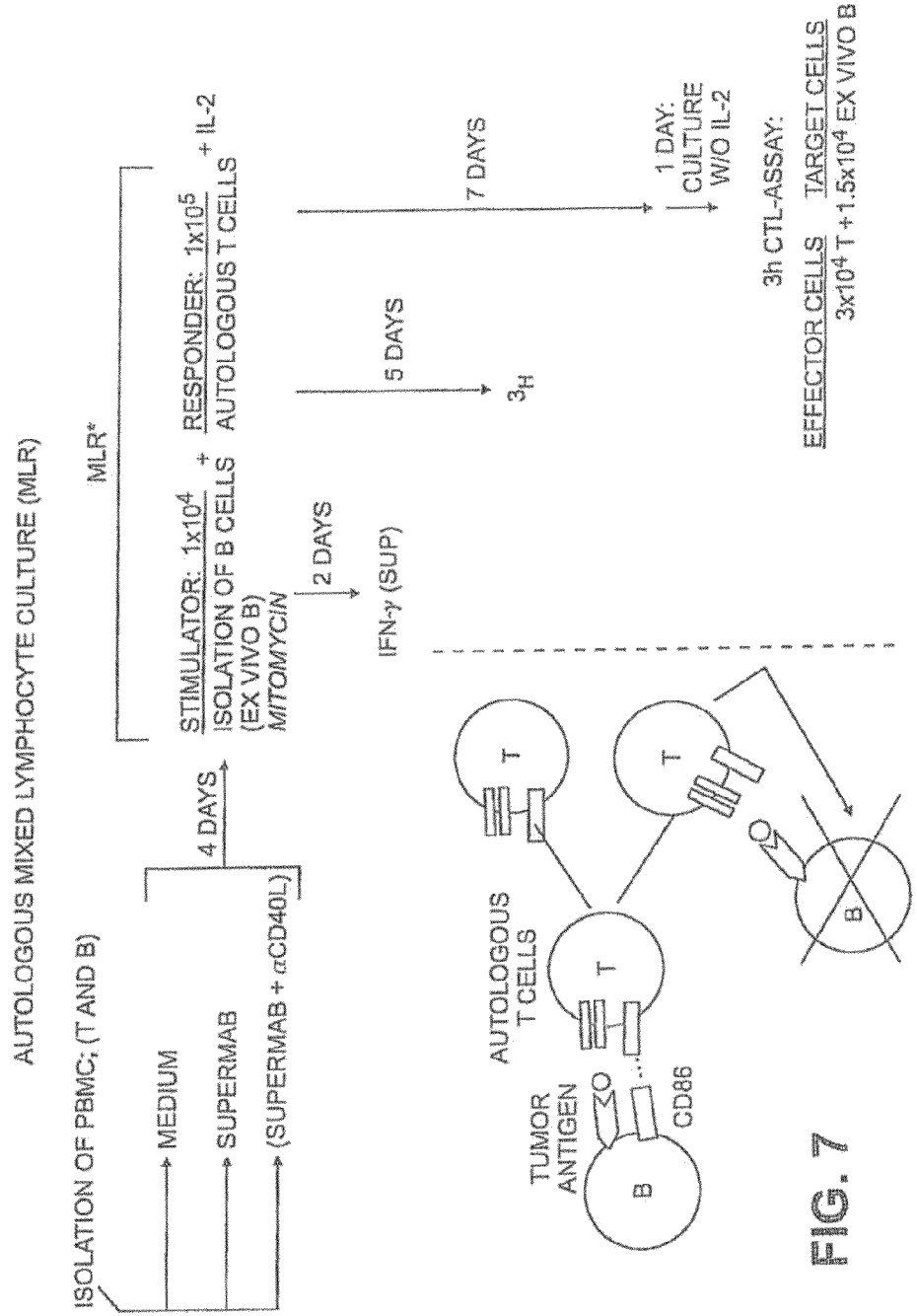
FIG. 7 is a diagrammatic representation showing stimulation cells cultivated with autologous cells in the presence of the cytokine, Interleukin 2.

The aim of the immune therapy for B-CLL patients is to activate autologous (i.e. originating within the body itself) tumor-specific T cells by improving the antigen-presenting function of the B-CLL B cells and to thus permit them to eliminate tumor cells (i.e. B-CLL B cells). By means of the so-called autologous mixed lymphocyte culture, the question was investigated whether SuperMAB has such properties. For this purpose, again PBMC's of a B-CLL patient were isolated and cultivated in medium or in presence of SuperMAB. The FACS analysis showed in this experiment, too, an induction of B7.1 and in particular B7.2 in the SuperMAB-treated B-CLL B cells. After three days the B-CLL B cells were isolated from these cultures by magnetic separation, treated with mitomycin C and then used as antigen-presenting stimulator cells in the following autologous mixed lymphocyte culture: 1×10^4 stimulator cells were cultivated with 1×10^5 autologous T cells (=responder cells) in the presence of the cytokine Interleukin 2, in order to answer the following questions (FIG. 7).

Figure 5:
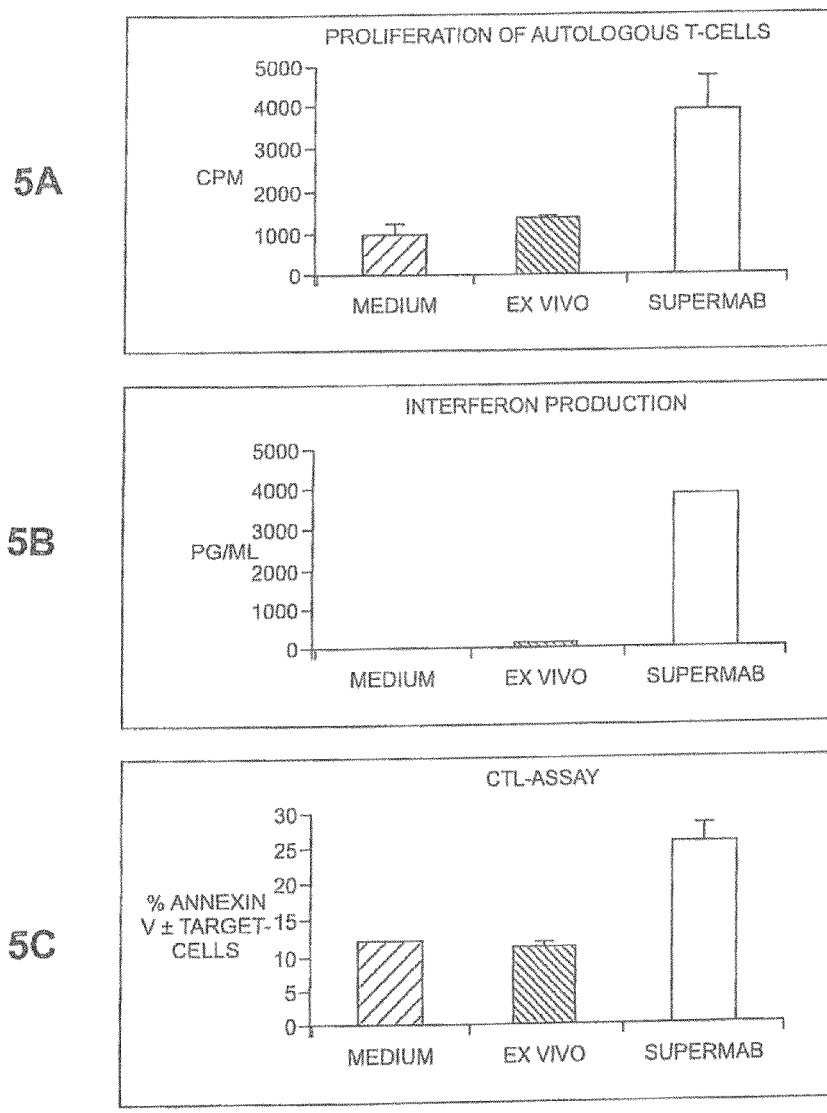
FIG. 5A-5C are graphical representations showing the effect of SuperMAB pretreatment on activation and proliferation of autologous T cells.

Are B-CLL B cells from the SuperMAB process capable to activate autologous T cells and drive them to proliferation? The test system was here the 3H thymidine incorporation. Result: compared to the medium/ex vivo processes, the proliferation of the autologous T cells could be increased by a factor of 4, because of the pretreatment with SuperMAB (FIG. 5a).

Can the thus activated T cells produce the cytokine interferon-gamma? Interferon-gamma is produced, among other sources, by so-called effector T cells. To the effector T cells belong the cytotoxic T lymphocytes, which are capable to eliminate tumor cells. The concentration of interferon-gamma in the cell culture supernatant was determined by means of ELISA. Result: whereas in the processes medium/ex vivo practically no interferon-gamma was produced, the responder T cells from the SuperMAB process could obviously be excited to the synthesis of this cytokine (FIG. 5b).

Are the activated T cells capable to eliminate autologous tumor cells? For answering this question, 3×10^4 responder T cells (=effector T cells in question) were isolated on day 8 of the mixed lymphocyte culture and cultivated for 3 hours with 1.5×10^4 freshly isolated B-CLL B cells (=target cells). Then the incubation with the protein annexin V and a monoclonal antibody with specificity for CD19 took place. By annexin V, to which a fluorescence dye is coupled, apoptotic cells (these are cells, which have died because of a programmed cell death) can be analyzed by flow cytometry. An induction by treatment with SuperMAB of potent tumor-specific effector T cells and an increased death of tumor cells resulting therefrom should therefore be accompanied by an increase of the percentage of annexin V-positive cells in the FACS analysis. Result: in this test, too, the SuperMAB process showed the best result: in the processes medium/ex vivo, about 12% of the target cells (=CD19+ tumor cells) could be stained with annexin V, in the SuperMAB process however more than 25% (FIG. 5c).

Figure 8:
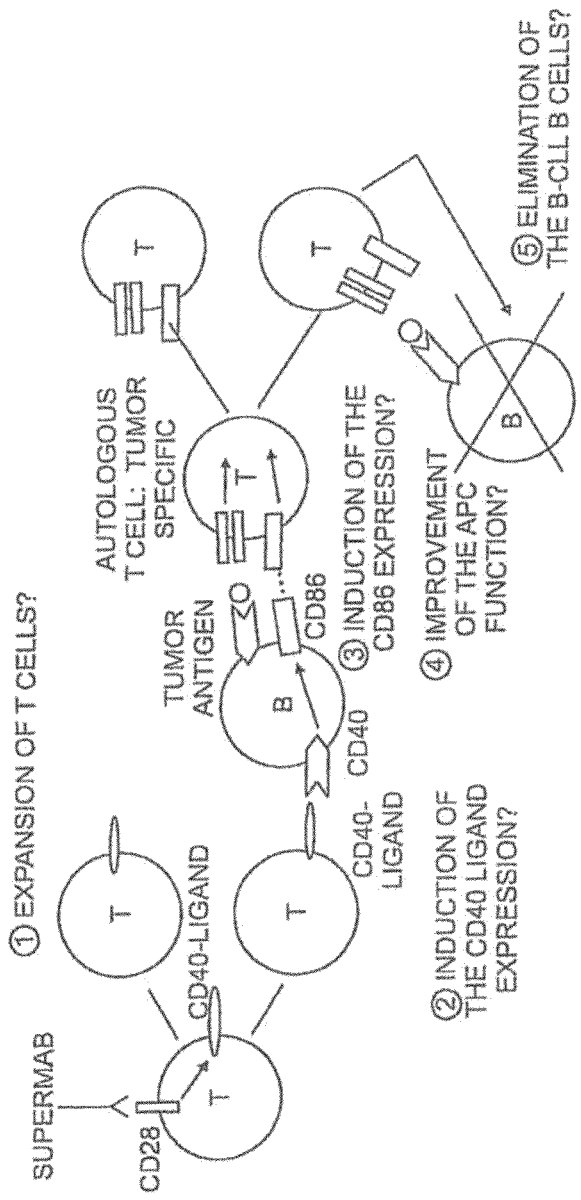
FIG. 8 is a diagrammatic representation of the mechanism for the use of SuperMAB to activate tumor-specific autologous T cells and to induce an elimination of tumor cells by an induction of costimulatory proteins on the surface of the antigen-presenting B-CLL B cells.

Obviously, by the use of SuperMAB, it is possible to activate tumor-specific autologous T cells and to induce an efficient elimination of the tumor cells. Presumably, the reason for this is an induction of costimulatory proteins on the surface of the antigen-presenting B-CLL B cells. The possible mechanism is diagrammatically shown in FIG. 8.

Example 6

Production of a Monoclonal Antibody TGN1412 According to the Invention

In the following, the production of a monoclonal antibody TGN1412 according to the invention is described, which consists of the amino acid sequences of the light and heavy chains cited in FIGS. 9a and 9b.

The DNA molecules cited in FIGS. 9c and 9d were synthesized in a way usual in this technology. The obtained cDNA's, respectively coding for the heavy and the light chain of the monoclonal antibody as indicated, were inserted into plasmids pLNOH and pLNOK. With regard to the method in detail, the plasmids and the interfaces, reference is made to the document Norderhaug et al., Journal of Immunological Methods, 204:77-87 (1997).

With the respective plasmids, *E. coli* cells were transformed. The transformed *E. coli* cells were multiplied, and the respective plasmids were obtained therefrom to a larger scale.

With the obtained respective plasmids, comprising the DNA information for the complete heavy or light chain, COST cells were transiently cotransfected, and CHO and NSO cells were stably cotransfected. The cotransfection was made in a usual way with Lipofectamine (Invitrogen) or Effectene (QIAGEN) according to the respective manufacturer's instructions.

The obtained transfected cells were cultivated in standard culture medium in CO2 incubators (5% CO2) at 37° C. in T flasks and roller bottles. Stably transfected cells, which express the intact antibody, were selected by means of G418 and hygromycin B selection. Stable transformants were then subcloned and further cultivated.

Cell culture supernatants with secreted antibodies were analyzed by means of activity assays, binding assays (FACS analysis), SDS-PAGE and Western blotting.

For purification, cell culture supernatants were guided over a protein A or protein G column, in order to specifically bind the desired antibodies. Bound antibodies were eluted with acidic buffer (0.1 M glycin, pH 3.0-3.4) and then neutralized with 1 M Tris (pH 8.0). The thus purified antibodies were dialyzed against PBS buffer and concentrated up according to requirements by means of membrane filtration, if applicable. The obtained antibodies were then used for proliferation assays, activity assays, binding assays (FACS analysis for binding to CD28-positive cells), ELISA, SDS-PAGE and Western blotting.

The invention claimed is:

1. A method for activating and expanding T cells in a cell suspension, comprising reacting the cell suspension with a superagonistic monoclonal antibody specific for CD28, wherein the cell suspension is prepared from a body fluid taken from a B-cell chronic lymphocytic leukemia (B-CLL) patient.

2. The method of claim 1, wherein the superagonistic monoclonal antibody specific for CD28 comprises a heavy chain variable region comprising the amino acid sequence set forth in SEQ ID NO: 26 or SEQ ID NO: 19.

3. The method of claim 1, wherein the superagonistic monoclonal antibody specific for CD28 comprises a light chain variable region comprising the amino acid sequence set forth in SEQ ID NO: 25.

4. The method of claim 1, wherein the superagonistic monoclonal antibody specific for CD28 comprises a heavy chain constant region comprising the amino acid sequence set forth in one of SEQ ID NO: 22, SEQ ID NO: 23, and SEQ ID NO: 24.

5. The method of claim 1, wherein the superagonistic monoclonal antibody specific for CD28 comprises a light chain constant region comprising the amino acid sequence set forth in SEQ ID NO: 21.

6. The method of claim 1, wherein the T cells are activated to express CD40 ligand (CD40L).

7. The method of claim 1, wherein the number of T cells is increased.

8. The method of claim 1, wherein the body fluid is blood.

* * * * *

SEQUENCE LISTING

```
<160> NUMBER OF SEQ ID NOS: 28

<210> SEQ ID NO 1
<211> LENGTH: 6
<212> TYPE: PRT
<213> ORGANISM: Artificial
<220> FEATURE:
<223> OTHER INFORMATION: human CD28 partial sequence

<400> SEQUENCE: 1

Val Tyr Ser Lys Thr Gly
1               5

<210> SEQ ID NO 2
<211> LENGTH: 4
<212> TYPE: PRT
<213> ORGANISM: Artificial
<220> FEATURE:
<223> OTHER INFORMATION: human CD28 partial sequence

<400> SEQUENCE: 2
```

Tyr Ser Lys Thr
1

<210> SEQ ID NO 3
<211> LENGTH: 5
<212> TYPE: PRT
<213> ORGANISM: Artificial
<220> FEATURE:
<223> OTHER INFORMATION: human CD28 partial sequence

<400> SEQUENCE: 3

Tyr Ser Lys Thr Gly
1               5

<210> SEQ ID NO 4
<211> LENGTH: 5
<212> TYPE: PRT
<213> ORGANISM: Artificial
<220> FEATURE:
<223> OTHER INFORMATION: human CD28 partial sequence

<400> SEQUENCE: 4

Val Tyr Ser Lys Thr
1               5

<210> SEQ ID NO 5
<211> LENGTH: 6
<212> TYPE: PRT
<213> ORGANISM: Artificial
<220> FEATURE:
<223> OTHER INFORMATION: human CD28 partial sequence

<400> SEQUENCE: 5

Tyr Ser Lys Thr Gly Phe
1               5

<210> SEQ ID NO 6
<211> LENGTH: 7
<212> TYPE: PRT
<213> ORGANISM: Artificial
<220> FEATURE:
<223> OTHER INFORMATION: human CD28 partial sequence

<400> SEQUENCE: 6

Val Tyr Ser Lys Thr Gly Phe
1               5

<210> SEQ ID NO 7
<211> LENGTH: 5
<212> TYPE: PRT
<213> ORGANISM: Artificial
<220> FEATURE:
<223> OTHER INFORMATION: human CD28 partial sequence

<400> SEQUENCE: 7

Ser Lys Thr Gly Phe
1               5

<210> SEQ ID NO 8
<211> LENGTH: 8
<212> TYPE: PRT
<213> ORGANISM: Artificial
<220> FEATURE:
<223> OTHER INFORMATION: human CD28 partial sequence

<400> SEQUENCE: 8

Gly Asn Tyr Ser Gln Gln Leu Gln
1               5

<210> SEQ ID NO 9
<211> LENGTH: 321
<212> TYPE: DNA
<213> ORGANISM: Artificial
<220> FEATURE:
<223> OTHER INFORMATION: mab 9D7 partial sequence

<400> SEQUENCE: 9
gatatccaga cgacacagac tacatcctcc cgttctgcct ctctgggaga cagagtcacc      60
atcagttgca gggcaggtca ggacattagt aattatttaa actggtatca gcagaaacca     120
gatggaactg ttaagctcct gatctactac acatcaagat tacactcagg agtcccatca     180
aggttcagtg gcagtgggtc tggaacagat tattctctca ccattagcaa cctggagcaa     240
gaagatattg ccacttactt ttgccaacag gtcatacgc ttccgtggac gttcggtgga     300
ggcaccaagc tggaaatcaa a                                               321

<210> SEQ ID NO 10
<211> LENGTH: 107
<212> TYPE: PRT
<213> ORGANISM: Artificial
<220> FEATURE:
<223> OTHER INFORMATION: mab 5.11A partial sequence

<400> SEQUENCE: 10

Asp Ile Gln Thr Thr Gln Thr Thr Ser Ser Leu Ser Ala Ser Leu Gly
1               5                   10                  15

Asp Arg Val Thr Ile Ser Cys Arg Ala Gly Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly His Thr Leu Pro Trp
                85                  90                  95

Thr Phe Gly Gly Gly Thr Lys Leu Glu Ile Lys
            100                 105

<210> SEQ ID NO 11
<211> LENGTH: 363
<212> TYPE: DNA
<213> ORGANISM: Artificial
<220> FEATURE:
<223> OTHER INFORMATION: mab 9D7 partial sequence

<400> SEQUENCE: 11
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttccaggaa acaaactgga gtggatgggc tacataagat acagtggtag tactagctac     180
aatccatctc tcaaaagtcg aatctctatc actcgagaca catccaagaa ccagttcttc     240
ctgcagttga attctgtgac tactgaggac acagccacat attactgtgc aagagattgg     300
ccgcgaccga gctactggta cttcgatgtc tggggcgcag ggaccacggt caccgtctcc     360
tca                                                                   363

<210> SEQ ID NO 12
<211> LENGTH: 121
<212> TYPE: PRT
<213> ORGANISM: Artificial
<220> FEATURE:
<223> OTHER INFORMATION: mab 5.11A partial sequence

<400> SEQUENCE: 12

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Arg Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Asp Trp Pro Arg Pro Ser Tyr Trp Tyr Phe Asp Val Trp Gly
            100                 105                 110

Ala Gly Thr Thr Val Thr Val Ser Ser
        115                 120

<210> SEQ ID NO 13
<211> LENGTH: 360
<212> TYPE: DNA
<213> ORGANISM: Artificial
<220> FEATURE:
<223> OTHER INFORMATION: mab 9D7 partial sequence

<400> SEQUENCE: 13
caggtccaac tgcagcagtc cggacctgag ctggtgaagc cggggacttc agtgaggatt      60
tcctgcgagg cttctggcta caccttcaca agctactata tacactgggt gaaacagagg     120
cctggacagg gacttgagtg gattggatgt atttatcctg gaaatgtcaa tactaactat     180
aatgagaagt tcaaggacaa ggccacactg attgtagaca catcctccaa cactgcctac     240
atgcagctca gcagaatgac ctctgaggac tctgcggtct atttctgtac aagatcacac     300
tacggcctcg actggaactt cgatgtctgg ggcgcaggga ccacggtcac cgtctcctca     360

<210> SEQ ID NO 14
<211> LENGTH: 120
<212> TYPE: PRT
<213> ORGANISM: Artificial
<220> FEATURE:
<223> OTHER INFORMATION: mab 5.11A partial sequence

<400> SEQUENCE: 14

Gln Val Gln Leu Gln Gln Ser Gly Pro Glu Leu Val Lys Pro Gly Thr
1               5                   10                  15

Ser Val Arg Ile Ser Cys Glu Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

```
Lys Asp Lys Ala Thr Leu Ile Val Asp Thr Ser Ser Asn Thr Ala Tyr
 65                  70                  75                  80

Met Gln Leu Ser Arg Met Thr Ser Glu Asp Ser Ala Val Tyr Phe Cys
                 85                  90                  95

Thr Arg Ser His Tyr Gly Leu Asp Trp Asn Phe Asp Val Trp Gly Ala
            100                 105                 110

Gly Thr Thr Val Thr Val Ser Ser
            115                 120

<210> SEQ ID NO 15
<211> LENGTH: 321
<212> TYPE: DNA
<213> ORGANISM: Artificial
<220> FEATURE:
<223> OTHER INFORMATION: mab 9D7 partial sequence

<400> SEQUENCE: 15
gacatccaga tgaaccagtc tccatccagt ctgtctgcat cccttggaga cacaattacc    60
atcacttgcc atgccagtca aaacatttat gtttggttaa actggtacca gcagaaacca   120
ggaaatattc ctaaactctt gatctataag gcttccaacc tgcacacagg cgtcccatca   180
aggtttagtg gcagtggatc tggaacaggc ttcacattaa ccatcagcag cctgcagcct   240
gaagacattg ccacttacta ctgtcaacag ggtcaaactt atccgtacac gttcggaggg   300
gggaccaagc tggaaataaa a                                             321

<210> SEQ ID NO 16
<211> LENGTH: 107
<212> TYPE: PRT
<213> ORGANISM: Artificial
<220> FEATURE:
<223> OTHER INFORMATION: mab 5.11A partial sequence

<400> SEQUENCE: 16

Asp Ile Gln Met Asn Gln Ser Pro Ser Ser Leu Ser Ala Ser Leu Gly
  1               5                  10                  15

Asp Thr Ile Thr Ile Thr Cys His Ala Ser Gln Asn Ile Tyr Val Trp
                 20                  25                  30

Leu Asn Trp Tyr Gln Gln Lys Pro Gly Asn Ile Pro Lys Leu Leu Ile
             35                  40                  45

Tyr Lys Ala Ser Asn Leu His Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Thr Tyr Pro Tyr
                 85                  90                  95

Thr Phe Gly Gly Gly Thr Lys Leu Glu Ile Lys
            100                 105

<210> SEQ ID NO 17
<211> LENGTH: 15
<212> TYPE: PRT
<213> ORGANISM: Artificial
<220> FEATURE:
<223> OTHER INFORMATION: human CD28 partial sequence

<400> SEQUENCE: 17

Gly Asn Tyr Ser Gln Gln Leu Gln Val Tyr Ser Lys Thr Gly Phe
  1               5                  10                  15
```

-continued

<210> SEQ ID NO 18
<211> LENGTH: 107
<212> TYPE: PRT
<213> ORGANISM: Artificial
<220> FEATURE:
<223> OTHER INFORMATION: mab 9D7 partial sequence

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105
```

<210> SEQ ID NO 19
<211> LENGTH: 120
<212> TYPE: PRT
<213> ORGANISM: Artificial
<220> FEATURE:
<223> OTHER INFORMATION: mab 5.11A partial sequence

<400> SEQUENCE: 19

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
        115                 120
```

<210> SEQ ID NO 20
<211> LENGTH: 19
<212> TYPE: PRT
<213> ORGANISM: Artificial
<220> FEATURE:
<223> OTHER INFORMATION: mab TGN1412 leader peptide

<400> SEQUENCE: 20

```
Met Gly Trp Ser Cys Ile Ile Leu Phe Leu Val Ala Thr Ala Thr Gly
1               5                   10                  15

Val His Ser
```

```
<210> SEQ ID NO 21
<211> LENGTH: 107
<212> TYPE: PRT
<213> ORGANISM: Artificial
<220> FEATURE:
<223> OTHER INFORMATION: mab TGN1412 constant region light chain

<400> SEQUENCE: 21

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 22
<211> LENGTH: 327
<212> TYPE: PRT
<213> ORGANISM: Artificial
<220> FEATURE:
<223> OTHER INFORMATION: mab TGN1412 constant region heavy chain variant
      1

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 23
<211> LENGTH: 328
<212> TYPE: PRT
<213> ORGANISM: Artificial
<220> FEATURE:
<223> OTHER INFORMATION: mab TGN1412 constant region heavy chain variant
      2

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220
```

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys Lys
                325

<210> SEQ ID NO 24
<211> LENGTH: 326
<212> TYPE: PRT
<213> ORGANISM: Artificial
<220> FEATURE:
<223> OTHER INFORMATION: mab TGN1412 constant region heavy chain variant
      3

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 25
<211> LENGTH: 107
<212> TYPE: PRT
<213> ORGANISM: Artificial
<220> FEATURE:
<223> OTHER INFORMATION: mab TGN1412 varianble region light chain

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105

<210> SEQ ID NO 26
<211> LENGTH: 120
<212> TYPE: PRT
<213> ORGANISM: Artificial
<220> FEATURE:
<223> OTHER INFORMATION: mab TGN1412 variable region heavy chain

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
            35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
```

<210> SEQ ID NO 27
<211> LENGTH: 1721
<212> TYPE: DNA
<213> ORGANISM: Artificial
<220> FEATURE:
<223> OTHER INFORMATION: mab TGN1412 light chain

<400> SEQUENCE: 27

```
ggtaccgggc cgacctcacc atgggatgga gctgtatcat cctcttcttg gtagcaacag      60
ctacaggtaa ggggctcaca gtagcaggct tgaggtctgg acatatatat gggtgacaat     120
gacatccact ttgcctttct ctccacaggt gtgcattccg acatccagat gacccagtct     180
ccatcctccc tgtctgcatc tgtaggagac agagtcacca tcacttgcca tgccagtcaa     240
aacatttatg tttggttaaa ctggtatcag cagaaaccag ggaaagcccc taagctcctg     300
atctataagg cttccaacct gcacacaggg gtcccatcaa ggttcagtgg cagtggatct     360
gggacagatt tcactctcac catcagcagt ctgcaacctg aagattttgc aacttactac     420
tgtcaacagg gtcaaactta tccgtacacg ttcggcggag ggaccaaggt ggagatcaaa     480
cgtgagtcgt acgctagcaa gcttgatatc gaattctaaa ctctgagggg gtcggatgac     540
gtggccattc tttgcctaaa gcattgagtt tactgcaagg tcagaaaagc atgcaaagcc     600
ctcagaatgg ctgcaaagag ctccaacaaa acaatttaga actttattaa ggaatagggg     660
gaagctagga agaaactcaa acatcaagat ttttaaatac gcttcttggt ctccttgcta     720
taattatctg ggataagcat gctgttttct gtctgtccct aacatgccct gtgattatcc     780
gcaaacaaca cacccaaggg cagaavtttg ttacttaaac accatcctgt ttgcttcttt     840
cctcaggaac tgtggctgca ccatctgtat tcatcttccc gccatctgat gagcagttga     900
aatctggaac tgcctctgtt gtgtgcctgc tgaataactt ctatcccaga gaggccaaag     960
tacagtggaa ggtggataac gccctccaat cgggtaactc ccaggagagt gtcacagagc    1020
aggacagcaa ggacagcacc tacagcctca gcagcaccct gacgctgagc aaagcagact    1080
acgagaaaca caaagtctac gcctgcgaag tcacccatca gggcctgagc tcgcccgtca    1140
caaagagctt caacagggga gagtgttaga gggagaagtg cccccacctg ctcctcagtt    1200
ccagcctgac cccctcccat cctttggcct ctgaccctt ttccacaggg gacctacccc    1260
tattgcggtc ctcagctca tctttcacct caccccctc ctcctccttg ctttaatta     1320
tgctaatgtt ggaggagaat gaataaataa agtgaatctt tgcacctgtg gtttctctct    1380
ttcctcattt aataattatt atctgttgtt ttaccaacta ctcaatttct cttataaggg    1440
actaaatatg tagtcatcat aaggcgcata accatttata aaaatcatcc ttcattctat    1500
tttaccctat catcctctgc aagacagtcc tccctcaaac ccacaagcct tctgtcctca    1560
cagtcccctg ggccatggta ggagagactt gcttccttgt tttccccccc tcagcaagcc    1620
ctcatagtcc tttttaaggg tgacaggtct tacagtcata tatccctttga ttcaattccc    1680
tgagaatcaa ccaaagcaaa ttcctgcagc ccgggggatc c                        1721
```

<210> SEQ ID NO 28
<211> LENGTH: 2551
<212> TYPE: DNA
<213> ORGANISM: Artificial
<220> FEATURE:
<223> OTHER INFORMATION: mab TGN1412 heavy chain

<400> SEQUENCE: 28

```
ggtaccgggc cgacctcacc atgggatgga gctgtatcat cctcttcttg gtagcaacag    60
ctacaggtaa ggggctcaca gtagcaggct tgaggtctgg acatatatat gggtgacaat   120
gacatccact ttgcctttct ctccacaggt gtgcattccg aggtgcagct ggtgcagtct   180
ggggctgagg tgaagaagcc tggggcctca gtgaaggtct cctgcaaggc ttctggatac   240
accttcacca gctactatat acactgggtg cgacaggccc tggacaagg cttgagtgg    300
attggatgta tttatcctgg aaatgtcaat actaactata tgagaagtt caaggacagg   360
gccaccctga ccgtagacac gtccatcagc acagcctaca tggagctgag caggctgaga   420
tctgacgaca cggccgtgta tttctgtaca agatcacact acggcctcga ctggaacttc   480
gatgtctggg gccaagggac cacggtcacc gtctcctcag gtgagtcgta cgctagcaag   540
cttttctgggg caggccgggc ctgactttgg ctggggcag ggagggggct aaggtgacgc   600
aggtggcgcc agccaggtgc acacccaatg cccatgagcc cagacactgg accctgcatg   660
gaccatcgcg gatagacaag aaccgagggg cctctgcgcc ctgggccag ctctgtccca   720
caccgcggtc acatggcacc acctctcttg cagcttccac caagggccca tccgtcttcc   780
ccctggcgcc ctgctccagg agcacctccg agagcacagc cgccctgggc tgcctggtca   840
aggactactt ccccgaaccg gtgacggtgt cgtggaactc aggcgccctg accagcggcg   900
tgcacacctt cccggctgtc ctacagtcct caggactcta ctccctcagc agcgtggtga   960
ccgtgccctc cagcagcttg ggcacgaaga cctacacctg caacgtagat cacaagccca  1020
gcaacaccaa ggtggacaag agagttggtg agaggccagc acaggaggg agggtgtctg  1080
ctggaagcca ggctcagccc tcctgcctgg acgcaccccg gctgtgcagc cccagcccag  1140
ggcagcaagg catgccccat ctgtctcctc acccggaggc ctctgaccac cccactcatg  1200
ctcagggaga gggtcttctg gattttccca ccaggctccg gcagccaca ggctggatgc   1260
ccctacccca ggccctgcgc atacaggggc aggtgctgcg ctcagacctg ccaagagcca  1320
tatccgggag gaccctgccc ctgacctaag cccacccaa aggccaaact ctccactccc    1380
tcagctcaga caccttctct cctcccagat ctgagtaact cccaatcttc tctctgcaga  1440
gtccaaatat ggtcccccat gcccatcatg cccaggtaag ccaacccagg cctcgccctc  1500
cagctcaagg cgggacaggt gccctagagt agcctgcatc cagggacagg ccccagccgg  1560
gtgctgacgc atccacctcc atctcttcct cagcacctga gttcctgggg ggaccatcag  1620
tcttcctgtt ccccccaaaa cccaaggaca ctctcatgat ctcccggacc cctgaggtca  1680
cgtgcgtggt ggtggacgtg agccaggaag accccgaggt ccagttcaac tggtacgtgg  1740
atggcgtgga ggtgcataat gccaagacaa agccgcggga ggagcagttc aacagcacgt  1800
accgtgtggt cagcgtcctc accgtcctgc accaggactg gctgaacggc aaggagtaca  1860
agtgcaaggt ctccaacaaa ggcctcccgt cctccatcga aaaaccatc tccaaagcca  1920
aaggtgggac ccacggggtg cgagggccac atggacagag gtcagctcgg cccacccctct  1980
gccctgggag tgaccgctgt gccaacctct gtccctacag ggcagccccg agagccacag  2040
gtgtacaccc tgcccccatc ccaggaggag atgaccaaga accaggtcag cctgacctgc  2100
ctggtcaaag gcttctaccc cagcgacatc gccgtggagt gggagagcaa tgggcagccg  2160
gagaacaact acaagaccac gcctcccgtg ctggactccg acggctcctt cttcctctac  2220
agcaggctaa ccgtggacaa gagcaggtgg caggagggga atgtcttctc atgctccgtg  2280
atgcatgagg ctctgcacaa ccactacaca cagaagagcc tctccctgtc tctgggtaaa  2340
```

-continued

```
tgagtgccag ggccggcaag cccccgctcc ccgggctctc ggggtcgcgc gaggatgctt    2400
ggcacgtacc ccgtctacat acttcccagg cacccagcat ggaaataaag cacccaccac    2460
tgccctgggc ccctgtgaga ctgtgatggt tctttccacg ggtcaggccg agtctgaggc    2520
ctgagtgaca tgagggaggc agagcggatc c                                   2551
```